United States Patent
Sharma

(10) Patent No.: US 6,235,239 B1
(45) Date of Patent: *May 22, 2001

(54) VIRUCIDAL AND BACTERICIDAL AGENT FOR USE IN THE DISINFECTION OF BIOLOGICAL FLUIDS

(75) Inventor: Yash P. Sharma, Vienna, VA (US)

(73) Assignee: Medicine and Applied Sciences, Inc., Sterling, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/212,698

(22) Filed: Mar. 14, 1994

Related U.S. Application Data

(63) Continuation of application No. 07/696,955, filed on May 8, 1991, now abandoned.

(51) Int. Cl.$^7$ ...................................................... A61L 2/08
(52) U.S. Cl. .................................... 422/28; 422/29; 435/2
(58) Field of Search ................................ 422/28–29, 34; 435/2

(56) References Cited

U.S. PATENT DOCUMENTS

| | | | | |
|---|---|---|---|---|
| 4,833,165 | * | 5/1989 | Louderback | 422/28 |
| 4,944,920 | * | 7/1990 | Rubinstein | 422/28 |
| 4,946,648 | * | 8/1990 | Dichtelmuller et al. | 435/2 |
| 4,971,760 | * | 11/1990 | Rubinstein | 435/2 |
| 5,019,402 | * | 5/1991 | Kross et al. | 435/2 |

OTHER PUBLICATIONS

Hicks et al. "Inactivation of HTLV–III/LAV–Infected Cultures of Normal Human Lymphocytes by Nonasynal–9 in Vitro" The Lancet, Dec. 21/28 1985, pp. 1422–1423.*

* cited by examiner

Primary Examiner—Lyle A. Alexander

(57) ABSTRACT

The subject invention relates to a composition for the disinfection of biological fluids and uses thereof. The composition contains an anionic surfactant, at least one non-anionic surfactants and a stabilizer provided it is to be used in the disinfection of samples to be subjected to laboratory tests. If the sample is to be disinfected for transfusion purposes, other chemicals are added to the three basic active ingredients. The invention also relates to methods of using the composition.

19 Claims, 1 Drawing Sheet

VIRUCIDAL AND BACTERICIDAL AGENT FOR USE IN THE DISINFECTION OF BIOLOGICAL FLUIDS

This is a continuation of application Ser. No. 07/696,955, filed on May 8, 1991, which was abandoned upon the filing hereof.

BACKGROUND OF THE INVENTION

1. Technical Field

The subject invention relates to a composition for the disinfection of biological fluids and uses thereof. The invention also relates to methods of using the composition.

2. Background Information

A major concern among laboratory personnel is the handling of potentially infected blood and other samples for the purpose of laboratory testing. Patient samples can be potentially hazardous to the persons handling or performing the laboratory tests since the samples are capable of transmitting infectious or disease-causing agents.

Since all patient samples must be considered potentially dangerous, the cost of protective measures continues to rise while the efficacy of these measures remains to be determined. (American Hospital Association, "AIDS/HIV Infection: Recommendations for health care practices and public policy," *AHA Report* (1988)).

Furthermore, another concern involves protecting those individuals receiving blood transfusions, as these individuals are particularly at risk of contracting blood-transmitted diseases. Current trends in the practice of transfusion medicine are focused on enhancing the sterility of donor blood, especially from the standpoint of blood-borne viruses (BBV). The application of high efficiency leukocyte-removal filters to remove cell-associated BBV from blood has been somewhat successful in both laboratory and clinical trials (Rawal et al., *Transfusion* 29:460–62 (1989); Rawal et al., *Blood* 76:2159–61 (1990); Gilbert et al., *Lancet* 1:1228–31 (1989); de Graan-Hentzen et al., *Transfusion* 29:757–60 (1990)). However, these filters are unable to remove cell-free virions from blood or plasma. Thus, leukocyte-depleted blood from infected donors may retain the potential of transmitting hepatitis B (HBV), hepatitis C (HCV) and human immunodeficiency virus (HIV) to transfusion recipients.

Chemicals that are stable at room temperature, is compatible with blood samples and other biological fluids, and can kill microorganisms and viruses effectively in a relatively short period of time and methods of using same, can be of great importance and value in the prevention against various deadly diseases including AIDS, Hepatitis and several others that can be transmitted via blood and biological fluids.

Extensive studies have demonstrated the effectiveness of various chemical agents on the activity and growth of viral, bacterial and other organisms including human immunodeficiency virus, herpes virus, and gonorrhea. These agents include surfactants, purines or pyrimidines with ribose moiety, plant alkaloids, and antimutant agents.

In particular, Nonoxynol-9 and other nonionic surfactants have been employed as virucidal agents, but their use in blood samples and biological fluids is not acceptable due to their red cell lysing properties, or hemolytic effect, and their ability to alter proteins, enzymes and several other parameters that need to be tested in the blood samples. In particular, it is well known in the medical art that while chemical surfactants like Brij-35, Nonidet-P 40 and Nonoxynol-9 are capable of inactivating viruses by acting on the cell surface, proteins, and lipid layers, these chemicals can also damage the red cell surface if allowed to react for a prolonged period of time.

The applicant has considered the following patents and submits that the present invention is neither disclosed nor suggested therein: U.S. Pat. No. 4,012,494, U.S. Pat. No. 3,912,450, U.S. Pat. No. 3,867,517, U.S. Pat. No. 2,889,243, U.S. Pat. No. 2,380,166, U.S. Pat. No. 4,314,997, U.S. Pat. No. 4,164,565, U.S. Pat. No. 4,613,501, U.S. Pat. No. 4,806,463, U.S. Pat. No. 4,675,159, U.S. Pat. No. 4,978,688, U.S. Pat. No. 4,412,985, U.S. Pat. No. 4,924,624, U.S. Pat. No. 4,923,815, U.S. Pat. No. 4,833,165, U.S. Pat. No. 4,855,064, U.S. Pat. No. 4,471,054, U.S. Pat. No. 4,481,189, U.S. Pat. No. 4,841,023, and U.S. Pat. No. 4,764,369.

All U.S. patents and publications referred to herein are hereby incorporated by reference.

SUMMARY OF THE INVENTION

The subject invention relates to a novel composition which may be added to biological fluid samples, for example, blood samples, in order to efficiently kill and thereby inactivate the viruses and/or bacteria present therein. In this manner, the sample may be safely handled by laboratory personnel during routine laboratory tests, or in the case of blood products, utilized for transfusion purposes. One of several advantages of the composition is that it does not alter the customary test results which must be performed on the biological sample. Additionally, it may be added to any type of container means, for example, a test tube, blood collection tube, petri dish, blood bag or bottle filter paper.

The composition of this invention which is to be used for the disinfection of a lab sample consists essentially of the novel combination of: an anionic surfactant, at least one non-anionic surfactant, and a stabilizer which is used for the fixation of the biological sample. The preferred anionic surfactant is Brij-35 and the preferred non-anionic surfactant is Nonoxynol-9 or Nonidet-P 40. The preferred stabilizer is glutaraldehyde.

The invention further relates to a method of disinfecting a biological sample which is to be subjected to testing consisting essentially of the steps of: a) adding the above composition to a container means; b) adding the biological sample to the composition; and c) inducing intimate contact between the composition and the sample for a required time of several minutes in order to effect disinfection of the biological sample.

The present invention also relates to a composition for use in the disinfection of a blood or blood component sample contained in a blood bag, wherein the composition destroys all bacteria and viruses present in the sample yet maintains the structural integrity of the cells present in the sample such that the sample can be used for a transfusion. The composition consists essentially of, in combination: an anionic surfactant, at least one non-anionic surfactant, a stabilizer, two salts, and two phosphates. The preferred anionic surfactant is Brij-35. The preferred non-anionic surfactant is Nonoxynol-9 or Nonidet-P 40, and the preferred stabilizer is sucrose. The preferred salts are sodium and potassium chloride, and the preferred phosphates are sodium and potassium phosphate.

The present invention also includes a method of disinfecting a blood sample or blood component sample contained in a blood bag, consisting essentially of the combination of steps of: a) introducing the disinfectant composition into a blood bag containing blood or a component thereof; b) mixing the composition with the blood or blood component sample at regular intervals in order to induce intimate contact between the sample and the composition and thereby kill the viruses and bacteria present in the sample; c) separating the cellular components from the supernatant wherein the supernatant contains non-cellular components; and d) subjecting residual material to an extraction technique for a sufficient number of times effective for the removal of the remaining disinfectant composition components which were not separated out in step (c).

As noted above, the anionic surfactant and non-anionic surfactant of the present invention lyse red blood cells (i.e., cause a hemolytic effect) when used independently. However, when the anionic surfactant, non-anionic surfactant and stabilizer of the present invention are used in combination, unexpected results are observed. In particular, not only is the biological sample of interest disinfected, but in the case of a blood or blood component sample, the cells maintain their structural integrity and can be used for transfusion purposes. Moreover, the composition does not alter the results of lab tests to which the biological sample may be subjected. Thus, the composition of the present invention has remarkable properties which are due to the inventive combination of the three active elements.

DETAILED DESCRIPTION OF THE INVENTION

Figure 1:
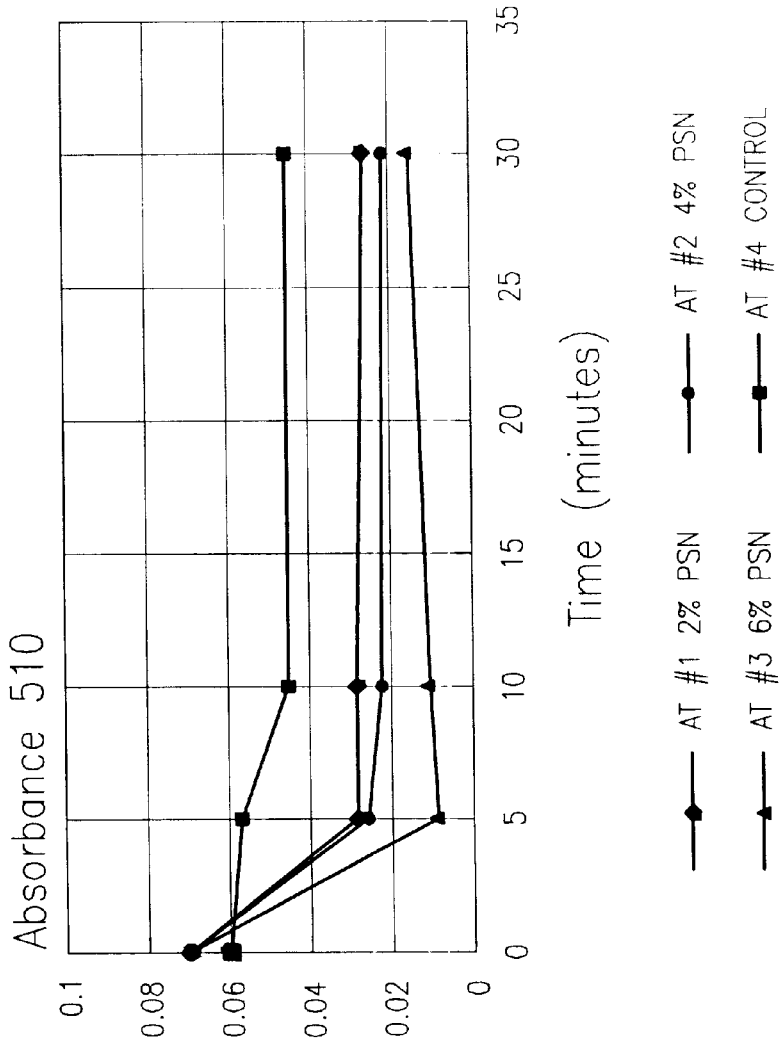
FIG. 1 represents the in vitro bacterial action of the inventive composition on *Yersinia enterocolitica*.

As noted above, the composition of the present invention has virucidal and bactericidal activity and may therefore be utilized to disinfect virtually any biological sample. Thus, a blood sample containing a pathogenic virus such as HIV, for example, may be rendered inocuous by adding the composition thereto. Thereafter, the sample could be reintroduced into a patient in need of a blood transfusion or could simply be tested, handled and disposed of by laboratory personnel without the risk of contracting the infection or disease caused by the virus or bacteria present in the sample.
Composition Used in the Disinfection of a Biological Sample to be Subjected to Laboratory Testing The composition used in the disinfection of a biological sample to be subjected to laboratory testing includes an anionic surfactant, a non-anionic surfactant and a stabilizer. These three agents may be added to a container means into which a biological sample has already been, or is about to be added. A suitable container includes, for example, a test tube or blood collection tube.

The anionic surfactant included in the composition may be, for example, a water soluble protein-compatible polyoxyalkylene ether or ester. Examples of such suitable compounds include: sulphated salts of oxyethylated alkylphenol, lauryl ether and sodium salts of dodecylbenzene sulfonate, 2-sulfoethyloleate, N-methyl-N-olylethanolsulfonate, dodecylsulfate, cholate, deoxycholate, and dodecyl-N-sarcocinate. Preferably, a reagent referred to as Brij-35 is utilized. Brij-35 is a lauryl ether. More specifically, it is referred to as polyoxyethylene-4-lauryl ether (i.e., $C_9H_{19}(OCH_2CH_2)_4OH$).

The non-anionic surfactant which is included in the composition may be, for example, dodecyldimethylbenzyl ammonium chloride, oxylethylated amine, hexadecyltrimethyl-ammonium chloride, dodecylpyrimidinium, tetradecyl ammonium bromide, or cetyltrimethyl-ammonium bromide. Two cationic surfactants which are particularly useful for purposes of the present invention are Nonidet-P 40 (NP-40) and Nonoxynol-9. Both of these chemicals are oxyethylated alkylphenols. The chemical name for NP-40 is octylphenol-ethyleneoxide. Its structure is as follows:

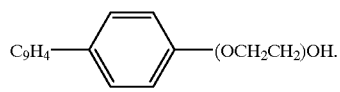

The chemical name for Nonoxynol-9 is poly(ethylene glycol)p-nonyl-phenyl-ether, and its structure is:

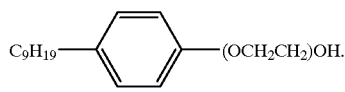

Two non-anionic surfactants may be added to the composition, if desired; however, only one such agent is required for the purpose of disinfecting the biological sample.

A stabilizer must also be present in the composition, in addition to the anionic and non-anionic surfactant. Examples of suitable stabilizers include aliphatic aldehydes, for example, glutaraldehyde and formaldehyde. Any aldehyde may be utilized which does not have an adverse effect on the results of conventional laboratory tests.

The purpose of the stabilizer is to temporarily fix (or stabilize) the red blood cells thereby allowing sufficient time for the composition to inactivate (i.e., kill) viruses and bacteria while keeping the red cells intact and undamaged.

The concentration of the anionic surfactant which should be utilized in preparing the composition is approximately 0.05–4%. (Concentration is calculated as gm reagent/100 ml aqueous solution.) Preferably, the cationic surfactant is used in a concentration ranging from 0.5–1.5%

Similarly, the concentration of the non-anionic surfactant which is utilized in the composition is approximately 0.05–4%. Preferably, a concentration of 0.5–1.5% is used.

The stabilizer should be used in a concentration ranging from approximately 0.000001–2.5%. The preferred range is 0.00001–0.001%.

In one embodiment of the composition described above, Brij-35 is used as the anionic surfactant, NP-40 as the non-anionic surfactant and glutaraldehyde as the stabilizer. This type of embodiment is to be utilized to disinfect a sample which is to be subjected to various laboratory tests and therefore has been added to a container means such as a test tube or blood collection tube. The Brij-35 and NP-40 are used in concentrations of 0.05–4% each, preferably in a concentration of approximately 0.5–1.5% each, and more preferably in a concentration of 1.0%. Glutaraldehyde is used as a stabilizer and is provided in a concentration of about 0.000001–2.5%, preferably in a concentration of 0.00001–0.001% and more preferably in a concentration of about 0.00005%.

Another embodiment of this composition contains Brij-35 as the anionic surfactant, Nonoxynol-9 as the non-anionic surfactant, and glutaraldehyde as the stabilizer. The Brij-35 and Nonoxynol-9 are again utilized in a concentration of about 0.05–4%, preferably in a concentration of 0.5–1.5% and more preferably in a concentration of approximately 1.0%. The glutaraldehyde is used in a concentration of about 0.000001–2.5%, preferably in a concentration of 0.00001–0.001%, and more preferably in a concentration of about 0.00005%. Again, this embodiment is to be used for a sample to be subjected to laboratory tests.

In another embodiment of the composition, Brij-35 is used as the anionic surfactant and two non-anionic surfactants, in particular, NP-40 and Nonoxynol-9 are utilized, in addition to a stabilizer such as glutaraldehyde. Brij-35, Nonoxynol-9 and Nonidet-P 40 are each used in a concentration of about 0.05–4%, preferably in a concentration of 0.5–1.5%, and more preferably in a concentration of approximately 1.0%. Glutaraldehyde is used in a concentration of about 0.000001–2.5%, preferably in a concentration of about 0.00001–0.001%, and more preferably in a concentration of about 0.00005%.

The above embodiments may be utilized with respect to the disinfection of a biological sample which is to undergo various laboratory tests. The compositions are not to be used to disinfect sample contained in blood bags. Glutaraldehyde is a toxic chemical and cannot therefore be added to blood or a blood component sample which is to be transfused into a mammal, in particular, a human.

The composition which is to be used to disinfect a sample about to undergo laboratory testing may either be used in a liquid or powder form.

One or more agents could also be added to the three active ingredients in order to create a composition which would be suitable for in vivo use. In particular, other reagents which could be included with the three active ingredients are, for example, octonanoxynol, Nonoxynol-9 spermicides, Resorcinol, Xanthine, Saffron and purified snake venoms, and ampholytic surfactants such as dodedcylbeta alanine, N-dodecylaminoethanesulfonic acid palmitoyllysolecithin and dodecyl-N-betaine. Optimal proportions of one or more of these agents would create a well-balanced composition which would be non-toxic and biocompatible.

Method of Using the Composition to Disinfect Laboratory Samples

The method of using the above-described composition to inactivate viruses and bacteria present in biological fluid samples which are to be tested is quite rapid and convenient.

The method of treating the biological sample (e.g., a blood sample) comprises the following steps:
a) adding the composition to the container means in which the biological sample is subsequently to be added;
b) adding the biological sample to the composition;
c) inducing contact between the composition and the sample for a required time of several minutes in order to effect disinfection of the sample.

Laboratory tests of interest may then be carried out, for example, cholesterol, glucose and potassium level tests as well as cell counts.

It is preferable to add the composition to the container means prior to the addition of the biological sample rather than subsequent to the addition of the sample. However, the sample may be added to the container means first, if desired. The sample and the composition must remain in contact for at least two minutes. However, contact may occur for up to several hours. Furthermore, the method is carried out at room temperature.

The "inactivated" sample may then be stored at room temperature for up to approximately 6 hours, and then at 4° C.

Again, the above method is to be utilized if it is desirable to test the biological sample of a patient. By inactivating the viruses or bacteria present in the sample, the sample does not thereafter pose a threat to the laboratory personnel carrying out the tests of interest. These individuals are otherwise suspectible to contracting infections or diseases which may be transmitted by the viruses and/or bacteria present in the untreated sample.

Furthermore, the composition will not affect conventional test results. Thus, such analytical results are therefore accurate, unaltered and remain reliable.

Composition Used in the Disinfection of a Blood Sample or Blood Component Sample Which is to be Transfused Into a Patient In an instance where the biological sample is blood or a component thereof is to be used for a transfusion, and a blood bag is therefore required, the three active ingredients of the composition (i.e., an anionic surfactant, a non-anionic surfactant and a stabilizer) are mixed with other reagents in order to create a solution which may then be mixed with the blood or blood component in question.

As described above, the anionic surfactant included in the composition may be, for example, a water soluble protein-compatible polyoxyalkylene ether or ester. Examples of such suitable compounds include: sulphated salts of oxy-ethylated alkylphenol, lauryl ether and sodium salts of dodecylbenzene sulfonate, 2-sulfoethyloleate, N-methyl-N-olylethanolsulfonate, dodecylsulfate, cholate, deoxycholate, and dodecyl-N-sarcocinate. Preferably, Brij-35 is used.

The non-anionic surfactant which is included the composition may be, for example, dodecyldimethylbenzyl ammonium chloride, oxylethylated amine, hexadecyltrimethyl-ammonium chloride, dodecylpyrimidinium, tetradecyl ammonium bromide, or cetyltrimethyl-ammonium bromide. Two non-anionic surfactants which are particularly useful for purposes of the present invention are Nonidet-P 40 (NP-40) and Nonoxynol-9.

Again, two non-anionic surfactants may be added to the composition, if desired; however, only one such agent is required for the purpose of disinfecting the biological sample.

A stabilizer must also be present in the composition, in addition to the anionic and non-anionic surfactant. Examples of suitable stabilizers include sugars, for instance, sucrose. The purpose of the stabilizer is again to temporarily fix or stabilize the red blood cells thereby allowing sufficient time for the composition to inactivate (i.e., kill) viruses and bacteria while keeping the red cells intact and undamaged.

The concentration of the anionic surfactant which should be utilized in preparing the composition is approximately 0.05–4%. Preferably, the cationic surfactant is used in a concentration ranging from about 0.5–1.5%

Similarly, the concentration of the non-anionic surfactant which is utilized in the composition is approximately 0.05–4%. Preferably, a concentration of about 0.5–1.5% is used.

The stabilizer should be used in a concentration ranging from approximately 0.01–5%. The preferred range is about 0.03–0.1%.

As mentioned above, in the case of blood or a blood product which is to be used in a transfusion and therefore has been placed in a blood bag, a solution must be added to the sample which includes other elements in addition to the anionic surfactant, non-anionic surfactant, and stabilizer. In particular, a buffer solution containing salts such as sodium chloride (NaCl) and potassium chloride (KCl) and phosphates, such as $Na_2HPO_4$ and $KH_2PO_4$, must be added to the three basic agents. These reagents provide an isotonic, isosmotic solution which aids in the stabilization of the red cells in the presence of sugars.

In one embodiment where the composition is to be used to disinfect a potentially transfusable blood or blood component sample, Brij-35 is provided as the anionic surfactant, NP-40 as the non-anionic surfactant and sucrose as the stabilizer. These three components are non-alkylating and non-carcinogenic according to FDA findings. Furthermore, the composition also contains NaCl and KCl, and two phosphates such as sodium phosphate or potassium phosphate. In particular, Brij-35 is used in a concentration of about 0.05–4.0% and NP-40 is also provided in a concentration of about 0.05%–4.0 and preferably in a concentration of 0.5–1.5% More preferably, a concentration of about 1.0% of each reagent is used. Sucrose is provided in a concentration of approximately 0.01–5% and preferably in a concentration of about 0.03–1% and more preferably in a concentration of about 0.05%. Sodium chloride is used in a concentration of about 0.4–5.0%, preferably in a concentration of about 0.5–1.5%, and more preferably in a concentration of about 0.90%. Potassium chloride is used in a concentration of about 0.01–5%, preferably in a concentration of about 0.02–1.0%, and more preferably in a concentration of about 0.04%. Sodium phosphate and potassium phosphate are each used in a concentration of about 0.01–5%, preferably in a concentration of about 0.05–3% and more preferably in a concentration of approximately 0.1%.

In another embodiment of the composition which is to be used to disinfect a sample for transfusion purposes, Nonoxynol-9 is used as the non-anionic surfactant in the composition rather than Nonidet-P 40. Brij-35 is used in a concentration of about 0.05–4.0%, preferably in a concentration of 0.5–1.5% and more preferably in a concentration of 1.0%. The ranges for the concentration of Nonoxynol-9 are equivalent. Sucrose is provided in a concentration of approximately 0.01–5%, preferably in a concentration of about 0.03–1% and more preferably in a concentration of 0.05%. Sodium chloride is used in a concentration of about 0.4–5.0%, preferably in a concentration of about 0.5–1.5%, and more preferably in a concentration of about 0.90%. Potassium chloride is used in a concentration of 0.01–5.0%, preferably in a concentration of 0.02–1.0%, and more preferably in a concentration of 0.04% Sodium phosphate and potassium phosphate are each used in a concentration of about 0.01–5%, preferably in a concentration of about 0.05–3% and more preferably in a concentration of approximately 0.1%.

In another embodiment to be used to disinfect a potentially transfusable blood sample, both Nonidet-P 40 and Nonoxynol-9 are added to the composition, in the ranges specified above. In particular, Nonoxynol-9 and Nonidet-P 40 are provided in a concentration of about 0.05%–4.0 each, preferably in a concentration of 0.5–1.5% and, more preferably, in a concentration of about 1.0% each. Sucrose is provided in a concentration of approximately 0.01–5%, preferably in a concentration of about 0.03–1% and more preferably in a concentration of 0.05%. Sodium chloride is used in a concentration of about 0.4–5.0%, preferably in a concentration of about 0.5–1.5%, and more preferably, in a concentration of about 0.90%. Potassium chloride is utilized in a concentration of 0.01–5.0%, preferably in a concentration of 0.02–1.0%, and more preferably in a concentration of 0.4% Sodium phosphate and potassium phosphate are each used in a concentration of about 0.01–5%, preferably in a concentration of about 0.05–3% and more preferably in a concentration of approximately 0.1%.

The composition which is to be added to a blood bag must be used in a liquid form.

Method of Using the Composition to Disinfect Blood or Blood Component Samples

As noted above, the second composition may be used to inactivate viruses and bacteria present in a blood sample (or blood component sample) which is to be introduced into a patient by way of transfusion.

In order to disinfect the transfusable blood or blood component, a method is carried out comprising the steps of:
  a) introducing the disinfectant composition into a blood bag, under sterile conditions, prior or subsequent to the addition of the blood or blood component;
  b) mixing the composition with the blood or blood component sample at regular intervals in order to induce contact between the sample and the composition and thereby kill the viruses and bacteria present in the sample;
  c) separating the cellular components from the supernatant wherein the supernatant contains non-cellular components; and
  d) subjecting the residual material to an extraction technique for a sufficient number of times in order to effect the removal of the composition which was not present in the supernatant of step (c).

The separation step may be accomplished by centrifuging the bag contents, removing the supernatant and then washing the remaining blood or blood component with a phosphate buffer saline solution (PBS) having a pH of approximately 7.4. The washing procedure is then carried out two more times. Separation may also be achieved by decantation or filtration as well. These processes may be carried out one or more times.

The extraction step of step d) may be carried out using an immunological or chromatographic technique or by any other conventional method.

The entire method may be carried out at room temperature. Furthermore, the sample and the disinfectant composition should remain in contact for at least 2 minutes but may remain in contact for several hours.

After the residual material of step d) is obtained, the following steps may be carried out:
  e) adding a preservative solution to the product of step (d); and
  f) storing the resulting product at 4° C.

The preservative solution may contain, for example, dextrose in a concentration of 2.2%, NaCl in a concentration of 0.9%, mannitol in a concentration of 0.75%, and adenine in a concentration of 0.27%. Such red cell preservative solutions are commercially available.

Using the above method, blood components may be disinfected for transfusion purposes. Thus, the recipient of the transfusion will not contract the disease or infection caused by the viruses and/or bacteria which may be present in the original donor sample. The recipient may, of course, be any mammal including a human.

Virucidal and Bactericidal Activity of the Composition

Several types of viruses and bacteria may be inactivated using the composition of the present invention. For example, the composition which is used to disinfect biological samples subjected to lab tests, and the composition used to disinfect a biological sample present in a blood bag, both may be used to inactivate several types of bacteria including, for example, cocci and bacilli. More specifically, both compositions may be used to inactivate gram positive bacteria, for example, *Mycobacterium tuberculosis,* gram negative bacteria, for example, *Yersinia enterolitica* and Chlamydia as well as acid fast bacteria.

*Y. enterocolitica* secretes an endotoxin that has causes severe pathological complications leading to death in a short period of time. The organism is normally present in the feces, thus, the composition of the present invention could be used to disinfect a fecal sample.

Both compositions may also be used to kill, for example, retrovirus, in particular, the human immunodeficiency virus (i.e., the AIDS virus), measles virus, togavirus, enterovirus, rhinovirus, rubella virus, reovirus, respiratory syncytial virus, cytomegalovirus, Epstein Barr Virus, Vesicular Stomatitis Virus, vaccinia virus, rabies virus, influenza virus, parainfluenza virus, measles virus, respiratory syncytial virus, reovirus, adeno-associated virus, lymphoma virus, human papovirus, lymphocytic choriomeningitis virus, parainfluenza virus, hepatitis B virus, and hepatitis (non-A and non-B) virus, hepatitis A virus, herpes simplex virus (type 1 & 2), and human papovirus.

In terms of the mechanism of action of the composition, it is thought that a synergistic effect results when the three components are mixed together and used in combination. In particular, when Brij-35 and NP-40 are mixed together, a new compound referred to as ocytl-ethylene-ether-oxide phenol is formed which inactivates the viruses and bacteria present in the biological fluid sample. Hemolytic effect (i.e., red cell lysing) is controlled by the stabilizing effect of the sugar (in the isotonic-isosmotic buffer).

Furthermore, it should be noted that several types of biological fluids may be disinfected utilizing the composition of the present invention in addition to those mentioned above. For example, in addition to blood, the composition may also be applied to samples containing urine, cerebrospinal fluid, plasma, serum, tissue, or organs or cells as used in tissue culture methods.

Additionally, the composition may be added to several types of container means in addition to a test tube or blood bag. For example, it may be added to a cup, blood collection tube, petri dish, or to any other collection device including bottle filter paper.

Furthermore, blood or blood components disinfected by the composition of the present invention may be used for diagnostic purposes, for producing reference controls, for producing standard solutions, and for producing plasma or serum based reagents. The composition itself may also be used to preserve biological samples by preventing microbial and viral growth which may occur in storage for a prolonged period of time.

The present invention can be illustrated by the use of the following non-limiting examples:

EXAMPLE I

Effect of Composition Concentrations on Hemolysis of Red Blood Cells

Finger puncture whole blood was dispensed in Normal Saline to give about 5% cell suspension. Whole blood was mixed by inversion to achieve uniform suspension. 1 ml cell suspension was dispensed in 12×75 plastic (polystyrene) tubes as indicated in Table I. 5%, 10%, and 20% dilutions of the concentrated composition (see composition B of Example XIV) were made in saline. An additional 20% dilution of the reagent was made to which 3 ml of P.S.P. (i.e., a solution with a high calcium concentration) was added. 0.1, 0.2, 0.5, and 1.0 ml of each dilution was added to each tube containing 1 ml of red cell suspension and mixed well by inversion. All tubes were read for hemolysis at 0, 5, 10, 30, 60 minutes and 2 through 6 hour at 1 hour intervals.

The hemolysis results are shown below in Table I:

TABLE I

| Tube # | 5% Red Cell in Saline | COMP. 5% | COMP. 10% | COMP. 20% | COMP. + PSP 20% | Time | % Hemolysis |
|---|---|---|---|---|---|---|---|
| 1 | 1 mL | 0.1 mL | | | | 0 min | 0 |
| 2 | 1 mL | 0.2 mL | | | | 5 min | 0 |
| 3 | 1 mL | 0.5 mL | | | | 10 min | 0 |
| 4 | 1 mL | 1.0 mL | | | | 15 min | |
| 5 | 1 mL | — | 0.1 mL | | | 1 hr | 0 |
| 6 | 1 mL | — | 0.2 mL | | | 2 hrs | 0 |
| 7 | 1 mL | — | 0.5 mL | | | 3 hrs | 0 |
| 8 | 1 mL | — | 1.0 mL | | | 4 hrs | 0 |
| 9 | 1 mL | — | — | 0.1 mL | | | 0 |
| 10 | 1 mL | — | — | 0.2 mL | | | 0 |
| 11 | 1 mL | — | — | 0.5 mL | | | 0 |
| 12 | 1 mL | — | — | 1.0 mL | | | 0 |
| 13 | 1 mL | — | — | — | 0.1 mL | | 0 |
| 14 | 1 mL | — | — | — | 0.2 mL | | 0 |
| 15 | 1 mL | — | — | — | 0.5 mL | | 0 |
| 16 | 1 mL | — | — | — | 1.0 mL | | 0 |
| 17 | 1 mL | — | — | — | — | | 0 |
| 18 | 1 mL | — | — | — | — | | 0 |
| 19 | 1 mL | — | — | — | — | | 0 |
| 20 | 1 mL | — | — | — | — | | 0 |

The above results show that the composition did not cause a hemolytic effect or red cell lysis for up to 6 hours.

EXAMPLE II

Effect of Composition Concentrations on Hemolysis of Red Blood Cells

The protocol of Example I was repeated using an old blood bag containing whole blood in Adsol (i.e., a red cell preservative solution (Baxter Pharmaceuticals)) and the composition in various concentrations as per Table I (see composition B of Example XIV). A set of tubes were included as controls to which none of the composition was added. All tubes were read for hemolysis at different time intervals for 24 hours, by centrifugation and visual observation.

No hemolysis was observed in all tubes and tubes containing the composition compared well with the control tubes. These findings were consistent with results of Experiment I. No red cell morphology abnormality was noted on examination under microscope.

EXAMPLE III

Hemolytic Effect of 1:1 Ratio of Composition to Whole Blood

An equal volume of the 100× composition (i.e., stock solution, see composition B of Example XIV) was added in a 1:1 ratio to a sample of whole blood (as used in Example II). Hemolysis was observed at different intervals, by centrifugation and visual observation.

No hemolysis was observed at time 0, 10 min., 20 min. using the concentrated composition. Gross hemolysis was observed at the 30 minute interval.

EXAMPLE IV

Determination of Hemolysis Using Test Tubes and Blood Bag

A fresh bag of donor whole blood which contained 430 ml. of blood in Adsol was spiked with ten logs of Vesicular Stomatitis Virus (V.S.V.) and thawed at room temperature. The virus was mixed well by rotation with the blood, and the bag was incubated for one hour at room temperature under continuous rotation and manual mixing. A sample of the virus/blood mixture was taken for use as a control at this stage.

The procedure of Example II was repeated using various concentrations of the composition (see composition B of Example XIV) and set aside for tissue culture to determine the efficacy of the agent on spiked blood with respect to tube testing.

110 ml. of 20% of the composition was added to the remaining blood in the bag, and the bag was rotated and manually mixed with the antiviral agent for 30 minutes. A sample was taken for virology testing. The bag was centrifuged for ten minutes, and the plasma was removed to separate the red cells. The cells were washed 4 times with normal saline.

No hemolysis was observed in any of the tube testing experiments.

No hemolysis was observed at the end of 3 saline washes of the bag. Some hemolysis was seen at the end of the 4th wash which was not produced in tube testing. Such hemolysis was not observed in repeat testing and washing of the bag 4 times. (Thus, the initial hemolysis may have been due to false results or a technical error.)

Tissue cultures were read after 48 and 72 hours. Two logs (99%) of virus killing was observed.

EXAMPLE V

Determination of the Antiviral Activity of the Composition on Whole Blood in Blood Containing ACD Anticoagulant A blood bag containing 370 ml of blood was mixed well by rotation and hand for 10 minutes. 50 ml portions were drawn using a syringe and transferred into 6 transfer blood bags under aseptic conditions. (The original bag was labelled as Bag #1 and other bags were numbered 2 to 7).

Bag #1 was kept to be used as a control, while other bags were used for various tests. Bag #2 was injected with 1 ml of HTLV III and was used as a positive control. Bag #3 was injected with 1 ml of HTLV III and used as a negative control. Bag #4 was injected with 1 ml of HTLV III and used as an untreated sample. Bag #5, #6 and #7 were used for other red cell viability tests.

5 ml samples of blood were drawn from each of the bags for tube tests run simultaneously with bag tests. All tubes were labelled the same as the bags. All bags were allowed to incubate at room temperature for over 60 minutes while mixing continuously on a shaker. Tubes were mixed by gentle vortexing. Bag #3 was then injected with 5 ml of the composition (see composition B of Example XIV). Tube 3 was treated identically. (All bags and tubes were treated the same throughout.)

All samples (bags and tubes) were tested for antiviral activity of the composition, red cell hemolysis, red cell enzymes B1 and B6, hemoglobin levels and K+ level in lysed red cells, using standard routine methods and tissue culture techniques.

Samples treated with the composition for up to 4 hours did not show the presence of hemolysis and compared well with samples that were not treated with the agent. This observation was made on the supernatant plasma after centrifugation, before washing steps were started. Tubes and bag samples were identical.

Saline (pH 5.6) washed samples did not show hemolysis after two washes. 1 hour after the third wash, pink coloration was noticed in bag samples but no coloration was seen in the tube samples.

Saline (pH 7.4) washed samples did not show hemolysis after two washes, and did not show any coloration up to 4 hours. Some degree of coloration was seen after 18 hours.

PBS (phosphate buffered saline, pH 7.4) washed samples behaved like saline (pH 7.4).

Hemoglobin levels of all samples treated or untreated with the agent were 14.9+/−0.7 mg/100 ml which compared to the control value of 15.0 mg/100 ml. Thus, the samples were accepted as unaltered.

B1 and B6 red cell enzymes tested on the lysed cells remained unaltered after treatment with the agent.

K+ values on the diluted red cell lysate were 4.3 meq/Lit on both treated samples and untreated samples.

Composition treated HTLV III samples gave $3.7 \times 10^6$ inactivation activity on samples tested after 3 washes with saline (pH 7.4) and $2.8 \times 10^5$ inactivation on samples before washing the cells (inactivation time 90 minutes).

Treated samples compared well with the untreated samples morphologically when examined under microscope.

Red cells stored with preservative for 31 days.

In conclusion, 4 log viral inactivation of HLTV III was achieved in 90 minutes using the above protocol. No hemolysis was observed for seven days, and all red cell parameters remained unchanged as compared with the controls.

EXAMPLE VI

The protocol of Example V was repeated using the composition described as composition B in Example XIV. The results obtained are as follows:

TABLE II

Composition Study - 24 Hour Exposure
All Results in terms of $TCID_{50}$/ml original suspension
Base VSV Input - Medium Positive Control > 6.3

| 0 Time Plasma | Viral Counts $°10^{7.25}$ | 0 Time RBC $10^{7.08}$ | — |
|---|---|---|---|
| | | Unwashed RBC Resuspended in 2 ml .9% saline | 4 Times Washed RBC Resuspended in .5 ml .9% saline |
| Plasma + 0.0 ml comp. | $10^{6.73}$ | $10^{5.68}$ | $10^{5.68}$ |
| Plasma + 0.1 ml 5% comp. | $10^{7.08}$ | $10^{5.85}$ | $10^{4.48}$ |
| Plasma + 1.0 ml 5% comp. | $10^{6.38}$ | $10^{5.85}$ | $10^{4.98}$ |
| Plasma + 1.0 ml 10% comp. | $10^{6.53}$ | $10^{5.15}$ | $10^{4.45}$ |
| Plasma + 1.0 ml 20% comp. | $10^{6.03}$ | $10^{5.33}$ | $10^{4.63}$ |

The above results as well as those of Example VII and Example VIII establish that greater than 2 log viral inactivation of VSV was achieved with two hour treatment with the composition at room temperature and 4° C. No hemolysis was observed, and red cell parameters were unaltered in comparison to the controls.

EXAMPLE VII

Determination of Plaque Forming Units Using Different Concentrations of the Composition Dilutions of the composition were created using a stock preparation (1/5, 1/10, 1/20, 1/100) (see composition B of Example XIV) and control (saline only). (The dilutions were made in 0.9% NaCl.) 3 mL of red blood cells, 3 mL of 0.9% NaCl, and 3 mL of the diluted composition were added to each test tube (i.e., 15 mL centrifuge tube).

The tubes were incubated for 2 hours at room temperature and at 37° C. 1 mL of the sample was collected for virus titration (VSV), and 1 mL of the sample was collected for hemoglobin/K+ measurement. Both samples were centrifuged to pack the cells, and the supernatant was collected. (The sample should promptly be assayed if possible, otherwise frozen). The samples were washed with saline twice (10 mL/wash). The cell pellets were re-suspended with Adsol to a final volume of 3 mL. They were then stored overnight. 2 mL of the sample to be used for the hemolysis/K+ measurement was collected and centrifuged. The supernatant was utilized for viral inactivation studies by tissue culture methods. 1 mL of the other tube was collected for virus titration.

The results obtained are shown in Table III below:

TABLE III

Plaque-forming unit measurements

| Composition Dilution | 25 C./2 hr. | 25 C./2 hr. + 24 hr. at 4 C. |
|---|---|---|
| | plaque-forming units/ml | |
| — | $4.2 \times 10^6$ | $3.1 \times 10^6$ |
| 1:5 | $2.8 \times 10^4$ | $3.4 \times 10^4$ |
| 1:10 | $>10^5$ | $>10^5$ |
| 1:20 | " | " |
| 1:100 | " | " |

EXAMPLE VIII

The same protocol as Example VII was used in order to obtain the results shown in Table IV. Plasma color reflects hemolysis. Red cell lysis gives a red-pink color.

TABLE IV

VSV data

| Drug Dilution | 25 C./2 hr. | 25 C./2 hr. + 24 hr. at 4 C. |
|---|---|---|
| | color of plasmas | |
| | clear | red |
| 1:5 | " | " |
| 1:10 | " | " |
| 1:20 | " | " |
| 1:100 | " | " |

EXAMPLE IX

The same protocols were used as in Example VII. The additional results obtained are shown in Table IV (cont.) as follows:

Sindbus Data

| Composition Dilution | 25 C./2 hr. | 25 C./2 hr. + 24 hr. at 4 C. |
|---|---|---|
| | plaque-forming units/ml | |
| 0 | $3.4 \times 10^6$ | $1.8 \times 10^5$ |
| 1:5 | $2.3 \times 10^4$ | $4.9 \times 10^3$ |
| 1:10 | $4.1 \times 10^4$ | $2.2 \times 10^4$ |
| 1:20 | TNTC | $3.6 \times 10^4$ |
| 1:100 | TNTC | $2.8 \times 10^4$ |
| 0 | clear | pink |
| 1:5 | " | red |
| 1:10 | " | " |
| 1:20 | " | " |
| 1:100 | " | pink (same as control) |

Greater than 2 log viral inactivation of VSV was achieved in two hour inactivation treatment with the composition (i.e., comp. A of Example XIV). No hemolysis of the red cells was observed at room temperature storage for two hours. Traces of red cell lysis were observed after 24 hours, storage at 4° C., in the presence of the composition.

EXAMPLE X

Inactivation of HIV using the Composition

The method of Example V was repeated using 4 different lots of HIV in concentrations of 4 logs added to freshly drawn 10 ml samples of nitrated whole blood. Virus and whole blood mixture was allowed to incubate for 3 hours with continuous mixing and agitation.

All examples were then treated with 1 mL of the composition (1/10 ratio) to give a final concentration of N.P-40 at 0.4% (see composition B of Example XIV).

Inactivation procedure was carried out for three hours at room temperature with continuous mixing.

All samples were washed three times with PBS, pH 7.4.

Total kill of HIV was achieved as shown by tissue culture zero growth using H-9 cells in all 4 red cell samples used for infecting host cells. Standard protocol was employed. No hemolysis was observed in all 4 samples after 3 washes with PBS pH 7.4. Cells were stored with 0.5 mL ringer preservative solution at 4° C. No hemolysis was observed at the end of 19 days. Red cell morphology remained unchanged at the end of 19 days test period.

EXAMPLE XI

Determination of the Effect of the Active Ingredients in the Composition on Red Blood Cells 0.1 mL of freshly drawn whole blood was diluted in 9.0 mL saline. 1 mL portions were then used for testing red cell fragility. The contents of the tubes were as follows:

Tube #1 Blood 1.0 mL+0.1 mL 10% NP-40

Tube #2 Blood 1.0 mL+0.1 mL 20% Brij-35

Tube #3 Blood 1.0 mL+0.05 mL 10% NP-40

Tube #4 Blood 1.0 mL+0.1 mL saline (control)

Red cell lysis was complete in both tubes containing NP-40 and Brij-35 within 10 minutes. Red cell lysis was complete in tube #3 within 15–20 minutes. However, no lysis was observed in control tube #4 for over 24 hours. Thus, the active ingredients in the composition, namely NP-40 and Brij-35, when used individually and without the stabilizers, were potentially damaging to the red cells as evidenced by complete hemolysis.

EXAMPLE XII

Testing of 5% Sucrose in Red Cell Diluent as Stabilizer of Red Cells in Presence of NP-40 and Bril-35

A fresh lot of the composition (see section B of Example XIV) was prepared. (An isotonic, isosmotic solution containing Na ions meq/L, K ions 4.5 meq/L, Cl ions 100 meq/L, osmolarity: 320 osmole/L, pH 7.4 was prepared. 5% sucrose was added to the diluent and used as a stabilizer for the composition with respect to the blood bag experiments.)

A 1:10 dilution of the composition preparation was made in red cell diluent containing 5% sucrose.

The protocol of Example XI was repeated to determine red cell lysis.

No red cell lysis was observed up to 6 hours. After 24 hours, approximately 1% hemolysis was seen.

In conclusion, when 5% sucrose was added to the composition (with a isotonic, iso-osmotic solution), it had a stabilizing effect on the red cells for up to six hours.

EXAMPLE XIII

Effect of Composition Containing 30% NP-40, 20% Brij-35 and Glutaraldehyde on Hemolysis The protocol of Example XI was utilized. A concentrated composition containing 20% NP-40+20% Brij 30 and glutaraldehyde gave substantial hemolysis after 30 minutes (see composition A of Example XIV). 1:5 and higher dilutions 1:10 and 1:20 did not lyse the red cell for over 24 hours. Substitution of 5% sucrose in red cell diluting fluid did not lyse the red cells for over 24 hours in 1:10 and 1:20 dilution of the composition without glutaraldehyde.

The above results establish that glutaraldehyde and sucrose have a red cell stabilizing effect when used with NP-40 and Brij-35.

EXAMPLE XIV

| Ingred. | Conc. (Final) | Range |
|---|---|---|
| A) Components of Sample Composition to be Used to Disinfect Sample to be Subjected to Laboratory Testing | | |
| NP-40 or (nonoxynol-9) | 1.0% | 0.05–4% |
| Brij-35 | 1.0% | 0.05–4% |
| Glutaraldehyde | 0.00005 | 0.000001–2.5% |
| B) Components of Sample Composition to be Used to Disinfect Sample to be Transfused | | |
| NP-40 (or nonoxynol-9) | 1.0% | 0.05–4% |
| Brij-35 | 1.0% | 0.05–4% |
| Sucrose | 0.05% | 0.01–5% |
| NaCl | 0.90% | 0.4–5% |
| KCl | 0.038% | 0.01–5% |
| Na$_2$HPO$_4$ | 0.142% | 0.01–5% |
| KH$_2$PO$_4$ | 0.136% | 0.01–5% |
| pH | 7.4 | 1–10 |

NP-40 Sigma CAT 1991, Page 1498, Nonidet P-40: Non ionic detergent (Octyphenoethyleneoxide) has 9 mole of Ethylenedi -oxide/mL of phenol). Its a hazy liquid or solid, viscosity 400–550 ops, pH 5.0.
Brij-35 Sigma CAT# 1991, Page 2000, Brij-35 23 Lauryl Ether. Non ionic surfactant and wetting agent (Polyoxyethylene-ether).
On mixing the two, a homogenous solution is obtained. This solution is then believed to form a new compound Octyl-ethylene-ether-oxide phenol is obtained which provides anti-bacterial and anti-viral action. Hemolytic action of this compound is controlled by the stabilizing effect of the sucrose and electrolyte buffer at pH 7.4.

C) Formulation of Stock Solution to be Used to Disinfect Sample to be Subjected to Laboratory Testing NP-40 was liquified by immersing the bottle in hot water until partially dissolved and broken into small lumps.

One liter of distilled water was added to a flask, the NP-40 was added, and the flask was placed over a hot plate magnetic mixer until the NP-40 was dissolved.

Brij-35 and Nonoxynol-9 were added and stirred continuously until all ingredients were dissolved so as to give a clear, homogenous solution. Glutaraldehyde was added. The final volume was adjusted to 5 liters with deionized water. Stirring was continued for 1 hr. The temperature was maintained at 45° C.

The formulation contained the following:

|  | | STOCK CONC. | WORKING CONC. |
|---|---|---|---|
| Nonoxynol-9 | 500 ml | 10% | 0.1% |
| NP-40 | 500 gm | 10% | 0.1% |
| Brij-35 | 1000 ml | 20% | 0.2% |
| 25% Glutar. | 10 ml | 0.005% | 0.00005% |
| Deion. H$_2$O QS to | 5000 ml | | |

The above components and concentrations were arrived at based on the results of Examples I-XIII.

EXAMPLE XV

Measurement of the Bactericidal Action of the Composition on Y. enterocolitica as Detected by Cell Lysis and Subcultures A clinical isolate of *Yersinia enterocolitica* was cultured in thioglycollate broth and kept in the incubator at 37° C. for 72 hours. It contained 3.0×10$^8$ viable bacteria per mL at this time point.

Separate culture vessels were prepared to contain 1.0%, 2.0%, 4.0% and 6.0% of the composition (see composition B of Example XIV) in thioglycollate broth. A control vessel without the composition contained the same volume of thioglycollate broth. Each vessel was inoculated with 6.0× 10$^7$ *Yersinia enterocolitica* to a total volume of 4.0 mL in each vessel.

The action of the composition in the respective vessels was monitored in a Spectronic-20 spectrophotometer by measuring absorbance at a wavelength of 510 nanometer at 0, 5, 10 and 30 minutes of holding the vessels at room temperature. Quintuplicate subcultures from each reaction vessel were prepared by spreading 10.0 microliters of each culture in blood agar plates after the 5 minute contact between the bacteria and the composition.

No growth was detected in the subcultures prepared from vessels in which the bacteria were exposed for 5 minutes to the composition (6.0%), but the bacteria grew out of inocula from vessels with 4.0% or less of the composition. (See FIG. 1.)

The above data indicates that the composition lysed $6.0 \times 10^7$ bacteria in 5 minutes and that this lytic action was bactericidal when the final concentration of the composition was 6.0% (v/v). It may be mentioned that this bactericidal concentration may be dependent on the inoculum size and for lower inocula it may be much less.

EXAMPLE XVI

Virus Inactivation Assay

The following materials were utilized in the procedure described below:

Donor Blood: Units of whole blood (WB) complying with the standards of the American Association of Blood Banks but with insufficient quantities for transfusion use, were purchased. Leukocyte-depleted blood (LDB) was obtained by filtering WB through a Pall leukocyte removal filter which yielded a filtrate containing less than 4 cells per mL blood (Rawal et al., *Blood* 76:2159–61 (1990)). Aliquots of WB and LDB were centrifuged at 800 g to collect respective cell-free plasma. Separate units were used for preparing the peripheral blood mononuclear cells (PBMC) feeder cells for coculture of HIV (Busch et al., *Am. J. Clin. Path* 88:673–80 (1987)).

Chemicals: Stock solution of the composition containing 20.0% Nonidet (NP-40) and 5.0% Nonoxynol-9 in a stabilized formulation was provided. (See composition B of Example XIV). The stock solution was diluted directly in whole blood (WB), plasma from whole blood (PWB), leukocyte-depleted blood (LDB) and plasma from LDB (PLDB) respectively for use in the virus inactivation assay (VIA).

Cell cultures: A clone of MT2 cells was provided and grown in RPMI. Peripheral blood mononuclear cells (PBMC) were isolated from donor blood and were stimulated by phytohemagglutinin (PHA, Sigma Chemical Co., St. Louis, Mo.) in RPMI over 48 hours at 37° C., to obtain PHA-PBMC for use in virus cocultures (Busch et al., supra (1987)).

Virus Stock and Inocula Standardization: Virus stock (strain $HTLV_{IIIB}$) was prepared in H9 cells growing in RPMI 1640 medium containing 10% fetal bovine serum and gentamicin (RPMI) (Busch et al., supra (1987)). Stock virus was titrated in MT2 cells in RPMI and found to contain $10^6$ syncytia forming units (SFU) per mL. Aliquots of the virus stock from a single batch, stored in liquid nitrogen, were used.

250 ul of 20.0% stock solution was mixed with WB, LDB, PWB and PLDB in sterile 12×75 mm polystyrene tubes, to obtain respective aliquots of 5.0 ml, each containing 2.0, 1.0, 0.5, 0.25, 0.125, and 0.0 percent of the composition. These were challenged by cell-free HIV with a standardized inoculum containing replication competent HIV equivalent to 10000 SFU or virions containing 83.47 picogram p24 antigen; each ml of the reaction mixture thus contained 200 SFU and 1 SFU which was equivalent to 0.41 picogram p24 antigen. All mixtures were held at room temperature for 1 hour and then centrifuged to remove red cells and/or other particulate matter. The supernatants from reaction mixtures containing 1.0% composition, as well as serial doubling dilutions (1:3–1:8 in RPMI) therefrom, were incubated with MT2 cells for 1 hour at 37° C. This step ensured that the contact between the residual virions from the reaction mixtures containing the composition (1.0%) and the MT2 host cells occurred in the presence of the sub-inactivation amounts of the composition, (i.e., 0.5% or less). Supernatants from the control mixtures were similarly processed. Following this contact, the host cells were washed thrice with RPMI and resuspended in 1.0 mL RPMI. These were next transferred to PLL-coated (Poly-L-Lysine, Sigma Chemical Co. Mo. Cat No. P1399) 24-well microtier plates (Nunc, Denmark) in quadruplicate wells so that each well had $0.5 \times 10^6$ MT2 cells. After one hour of contact for cell adhesion to the wells, the volume in each well was made up to 1.0 mL in RPMI. Following incubation at 37° C. for 5 days in an atmosphere of 5% carbon dioxide, the MT2 cells were scored for syncytia formation, HIV DNA by the polymerase chain reaction (PCR), and intracellular p24 antigen by an immunocytochemical staining procedure. Culture supernatants were also tested for p24 antigen by ELISA (Du Pont Co., Boston, Mass.).

Similarly, VIA was also performed using PHA-PBMC as the host cells instead of the MT2 cells. These were maintained in RPMI with 10% fetal bovine serum containing $2 \times 10^6$ fresh PBMC as feeder cells on a weekly schedule at 37° C. These cultures were monitored for 30 days with weekly sampling of the cells for the detection of p24 antigen and HIV DNA-bearing cells. A typical protocol using the composition (1.0%) in the reaction mixtures is shown in Table V, below. On the basis of PCR, therefore, the true HIV inactivating concentration of the composition was determined to be 2.0% under the above test conditions.

TABLE V

Experimental design for in vitro HIV inactivation assay by the composition (1.0%) in blood and plasma (1 hr. contact)

| Rxn. Vessels | A | B | C | D | E | F |
|---|---|---|---|---|---|---|
| HIV Inoculum (ul) | 100 | 100 | 100 | 100 | 100 | 100 |
| Composit. (ul) | 250 | 250 | 250 | 250 | 0 | 0 |
| Whole Blood (ul) | 4650 | 0 | 0 | 0 | 4900 | 0 |
| Leukocyte Depleted Bl. (ul) | 0 | 4650 | 0 | 0 | 0 | 4900 |
| Whole Blood Plasma (ul) | 0 | 0 | 4650 | 0 | 0 | 0 |
| Leuk. Depl. Blood Plasma (ul) | 0 | 0 | 0 | 4650 | 0 | 0 |

The inactivation assay showed that the composition, in concentrations below 0.5%, did not inactivate cell-free HIV (10,000 SFU) in 1 hr. of contact at room temperature. Thus, the presence of a 0.5% concentration of the composition in the reaction mixture during the contact time with MT2 cells did not interfere with the absorption of replication-competent virions to the cells. The same virus, inoculum, however, was inactivated by the composition (1.0%), as determined by two of the three marker tests for HIV (see Table VII below). HIV DNA was detected in the cells from the cultures of the several reaction mixtures with the composition in a concentration up to 1.0% but not with 2.0%. The inactivation of HIV by the composition (2.0%) was thus confirmed by the concurrent absence of syncytia formation, p24 antigen, and HIV DNA in the cultures from the reaction mixture containing 10,000 SFU of HIV and a 2.0% concentration of the composition. The control inoculum produced HIV positive signal in the tests listed in Table VII (below).

To determine whether or not the absence of residual replication-competent virus in the reaction mixtures reflected the inactivation of the inoculum by the composition, and not the potential interference by the test compound during the virus recovery stage, each mixture (Table V, A–F) was diluted two-fold in the range of 1:2–1:8 in RPMI before contacting with PHA-PMBC or MT2 cells for the adsorption. This step ensured that the contact between the host cells and the putative virions that survived the action of the composition (1.0%) occurred only in the presence of 0.5% or less of the composition which was earlier found not to inactivate HIV (see Table VI, below). The absence of syncytia formation, and p24 antigen from the culture supernatants and cells (Table VII), therefore point to the absence of the replication competent virions in mixtures treated with the composition (1.0%) in WB, LDB, WBP, and LDBP (mixtures A–D). Cell cultures from the control mixture (E,F) however showed the presence of syncytia formation and p24 antigen. Table VII also shows the absence of HIV DNA-bearing cells only in the cell cultures from the mixture treated with the composition (2.0%). On the basis of the polymerase chain reaction (PCR), therefore, the true inactivation concentration of the composition was determined to be 2.0% under the above test conditions.

TABLE VI

In vitro inactivation of HIV in whole blood, leukocyte-filtered blood and respective plasma in 1 hour at room temperature by the composition.
HIV attribute Composition (%) in the Reaction Mix

| | 2.0 | 1.0 | 0.5 | 0.25 | 0.125 | 0.0 |
|---|---|---|---|---|---|---|
| Synctia formulation | − | − | + | + | + | ++ |
| p-24-bearing cells | − | + | + | + | + | ++ |
| HIV DNA-bearing cells | − | +[a] | + | + | + | ++ |

(+) = positive, (−) = negative  [a] = cells in 50% of replicate wells were positive for HIV DNA.

TABLE VII

Evaluation of in vitro inactivation of HIV by the composition (1.0%) in whole blood, leukocyte-depleted blood, plasma from whole blood and plasma from leukocyte-depleted blood.
HIV detection criteria in MT2 cells and PBMC

| Cultures of reaction mixtures* | Syncytia in MT2 cells | | | p24 antigen intracellular | | | HIV DNA in cells cultured from reaction mixture |
|---|---|---|---|---|---|---|---|
| Dilutions tested 1: | 2 | 4 | 8 | 2 | 4 | 8 | NA |
| (A) | − | − | − | − | − | − | − |
| (B) | − | − | − | − | − | − | − |
| (C) | − | − | − | − | − | − | − |
| (D) | − | − | − | − | − | − | − |
| (E) | + | + | + | + | + | + | + |
| (F) | + | + | + | + | + | + | + |

(**) see table IV,
(+) = present,
(−) = absent,
NA = not applicable

EXAMPLE XVII

Validation of Virus Inactivation Assay

The efficiency of VIA was measured by quantitating p24 antigen in the supernatants of the reaction mixtures containing the control virus inoculum and MT2 cells in order to determine the extent of cell adsorption of the replication-competent virions in the inoculum treated under the conditions of VIA. (The presence of p24 antigen is indicative of all strains of HIV.)

"Heat-inactivated" inocula of HIV prepared by holding the virus stock suspension at 37° C. for 4 hours, were contacted with MT2 cells under the conditions of VIA. By quantitating the p24 antigen in the supernatants of cell cultures inoculated with "heat inactivated HIV", the extent of adsorption of replication-non-competent HIV by MT2 cells was measured. The p24 antigen was titrated in the respective wash solutions of MT2 cells exposed to these inocula in VIA to measure the efficiency of the two washes for the concurrent removal of the composition (see section B of Example XIV).

Table VIII (below) shows that only 0.07% of the p24 antigen from the replication competent virus (stock virus) was detectable in the supernatant. This indicates that 99.93% of the inoculated virus was adsorbed by $0.5 \times 10^6$ MT2 cells. In contrast, the heat-inactivated (replication non-competent) virus was not taken up by the MT2 cells; 99.03% of p24 antigen in the heat inactivated inoculum was recovered in the supernatant. Table VIII shows that after two washes p24 antigen was not detectable in the supernatant of the cultures from mixtures inoculated with heat-inactivated HIV.

TABLE VIII

Differential adsorption of replication competent and heat-inactivated (replication non-competent) HIV by NT2 cells in 1 hour at 37° C.

| | | | p24 antigen/ml (% input antigen) | |
|---|---|---|---|---|
| Stock Virus | | Input | Recovered | |
| | Wash | Reaction | I wash | II |
| Control | 61600 | 39.06(0.07) | 0.0 | 0.0 |
| Heat-Inactivated | 61600 | 61001.3(99.03) | 598.7(0.97) | 0.0 |

EXAMPLE XVIII

Biocompatibility of the Composition in vitro and Stability of the Composition in Treated Blood The composition (see composition B of Example XIV), in concentrations of 0.0, 0.5%, 1.0% and 2.0%, was added to 50.0 mL aliquots of WB and LDB respectively. After 1 hour at room temperature, these were centrifuged at 800 g to discard the supernatant containing the composition. Following three washes with sterile phosphate buffered saline, the packed cells in each reaction vessel were restored to 50.0 mL in ADSOL (Baxter Healthcare, Illinois). These were evaluated for total cell counts, hemoglobin, hematocrit, and mean corpuscular volume in an automated cell counter (Baxter Instruments Allentown, Pa.). Samples of blood stored for 20 days in the refrigerator were tested for red cell deformity at 290 um using ectacytometry.

The treated blood retained normal hematological parameters comparable to the untreated control blood. With respect to stability, the results shown in Table IX (below), demonstrate that the composition in virucidal concentrations did not adversely affect the cellular components of blood.

TABLE IX

Hematological data on packed cells prepared from whole blood treated with the composition in vitro.

| | Control | Composition(%) in blood over 1 hour treatment | | |
|---|---|---|---|---|
| Parameter | 0.0 | 0.5 | 1.0 | 2.0 |
| Leukocytes × $10^3$/cmm | 5.0 | 5.1 | 5.2 | 5.2 |
| Erythrocytes × $10^6$/cmm | 3.5 | 3.4 | 3.3 | 3.3 |
| Hemoglobin g/DL | 13.5 | 13.8 | 13.7 | 13.6 |
| Hematocrit % | 38.5 | 37.6 | 39.1 | 38.5 |
| MCV cu micron | 108.0 | 108.0 | 108.0 | 109.0 |
| Red cell deformability Ectacytometry (290 nm)* | 0.565 | 0.585 | 0.585 | 0.590 |

*after 20 days of storage in the refrigerator.

TABLE X

Hematological Tests on Composition Treated Blood Stored in Adsol for 39 Days in Refrigerator

| | Tests for red cell stability | | | |
|---|---|---|---|---|
| Treatment of Blood (1 hr) | Ectacytometer stress test (290 nm) | RBC × (million/ml) | HgB GMS/DL | HCT (%) |
| Untreated control | 0.545 | 3.40 | 11.8 | 36.1 |
| Composition | | | | |
| 0.5% | 0.535 | 3.36 | 11.6 | 35.1 |
| 1.0% | 0.545 | 3.36 | 11.8 | 35.6 |
| 2.0% | 0.535 | 3.37 | 11.9 | 35.9 |

EXAMPLE XIX

Antiviral Test on HIV and Hepatitis in Serum

Serum and whole blood (citrated and heparinized) samples (5 mL) negative by radioimmunoassay, Western blot and by enzyme immunoassay (EIA) tests for HIV and viral hepatitis, respectively, were each spiked separately with 0.5 mL of 200 $TCID_{50}$ containing $10^6$ infectious particles (IP) HIV and hepatitis A virus. ($TCID_{50}$, median tissue culture infective dose is that quantity of a virus which will produce a cytopathic effect in 50% of the cultures inoculated.) After a 24-hr. incubation at 37° C., 0.2-mL portions were withdrawn, treated with 10 uL of the composition (see composition A of Example XIV), and mixed gently. All samples were then used to infect H-9 cells. The cells were incubated with RPMI media for three weeks, then stained using the standard direct fluorescence procedure. The samples containing the composition (see composition A of Example XIV) showed no evidence of HIV or hepatitis A. The stains were identical to those of viral materials inactivated by standard methods of treatment with long-wavelength ultraviolet radiation and derivatives of psoralen, indicating that the composition was an equally potent virucidal agent. Viral identification by neutralization was not performed.

EXAMPLE XX

Evaluation of HIV Inactivation in Whole Blood

Three sets of eight samples, prepared as indicated in Example XVI, were incubated for 1, 5 and 10 min at the Table XI (below) levels of composition (see composition A of Example XIV) indicated.

After inoculation, the flasks were incubated at 37° C. and fed with growth media twice a week. After three weeks, the H-9 cells were fixed to slides for an indirect immunofluorescence assay. For the assay, a mouse anti-HIV p17 monoclonal antibody and an FITC-tagged rabbit anti-mouse conjugate were used. Slides were read on a fluorescence microscope and scored according to guidelines issued by the Centers for Disease Control (CDC) (Atlanta, Ga.).

Incubating 100 uL of the composition for 1 minute in 1 mL of heparinized blood was not sufficient to inactivate 100 uL ($10^5$ IP of HIV-1 virus).

The incubation of 100, 50, or 25 uL of the composition for 5 to 10 minutes was sufficient to inactivate $10^5$ IP of HIV-1. (See Table XII below).

TABLE XI

Schedule for HIV Inactivation study
20 × HIV-1[a]

| Tube No. | Heparinized blood (mL) | concentrate (uL) | Composition (uL) | THE[b] buffer(uL) |
|---|---|---|---|---|
| 1 | 1 | 100 | 100[c] | 500[d] | 0 |
| 2 | 1 | 100 | 50 | 200 | 0 |
| 3 | 1 | 100 | 25 | 100 | 0 |
| 4 | 1 | 100 | 12.5 | 50 | 0 |
| 5 | 1 | 100 | 6.25 | 25 | 0 |
| 6(Positive Control) | 1 | 100 | 0 | 0 | 0 |
| 7(Negative Control) | 1 | 0 | 0 | 0 | 0 |
| 8(Composition Control) | 1 | 0 | 100 | 500 | 0 |

[a]20 × HIV-1 concentrate contains $10^6$ HIV-1 infectious particles (IP) per ml.
[b]TNE is a buffer mixture of Tris, sodium, chloride and ethylene diamine tetraaceteic acid (EDTA).
[c]Samples in column A were incubated for 1 minute at room temperature before being used to inoculate duplicate flasks of H-9 cells.
[d]Samples in column B were incubated for 3 minutes at room temperature prior to inoculation of H-9 cells.

TABLE XII

Results of HIV Inactivation study

| Incubation | 1 min | | 5 min | | 10 min | | Tube | 3 min | |
|---|---|---|---|---|---|---|---|---|---|
| flask no. | 1a | 1b | 2a | 2b | 3a | 3b | No | 4a | 4b |
| Tube 1A | 2+ | 2+ | — | — | — | — | 1B | — | — |
| 1A | 3+ | 3+ | — | — | — | — | 2B | — | — |
| 3A | 3–4+ | 3–4+ | — | — | — | — | 3B | 1+ | 1+ |
| 4A | 3–4+ | 3–4+ | 1+ | — | — | — | 4B | 2+ | 1–2+ |
| 5A | 3–4+ | 3–4+ | 1–2+ | 1–2+ | 1–2+ | 5B | 2–3+ | 2–3+ |
| 6A | 3–4+ | 3=4+ | 3–4+ | 3–4+ | 3–4 | 6B | 3–4+ | 3–4+ |
| 7A | — | — | — | — | — | — | 7B | — | — |
| 8A | — | — | — | — | — | — | 8B | — | — |

(No cellular toxicity present)
[a]Grading intensity
4 + Glaring fluorescence
3 + Bright fluorescence
2 + Dull fluorescence
1 + Very dim fluorescence
— No fluorescence

EXAMPLE XXI

Hematological Studies

Whole blood collected in lavender-topped 7-mL tubes was well mixed and analyzed for routine complete blood counts (CBCs) and differential counts. The specimen was again mixed well and 2-mL portions aliquotted in two clean glass tubes; 10 μL of the composition (see composition A of Example XIV) were added to one of the two tubes and both tubes mixed for 10 min using a rotary-type inversion mixer. Both tubes were analyzed on a Coulter counter (Hialeah, Fla.) for the same parameters. Blood films prepared at the same time were stained with Giemsa stain for differential counts and red blood cell (RBC) morphology. The raw data are recorded in Table XIII. By inspection, no differences in results were evident between the specimens containing the composition and those without. Paired t-tests run on the results indicate no differences in population at the 0.05 level.

TABLE XIII

Effect of the composition on hematological values

| Test analyte name | Value after treatment with Composit. | Control Value |
|---|---|---|
| WBC × 10$^3$ | 8.1 | 8.1 |
| | 5.0 | 4.9 |
| | 7.2 | 7.1 |
| | 10.9 | 11.1 |
| | 5.5 | 5.5 |
| RBC × 10$^6$ | 7.1 | 7.2 |
| | 6.2 | 6.1 |
| | 5.1 | 5.1 |
| | 4.6 | 4.6 |
| | 6.1 | 6.1 |
| Hgb$^a$g/dL | 16.2 | 16.1 |
| | 13.6 | 13.2 |
| | 14.1 | 14.2 |
| | 11.7 | 11.8 |
| | 17.1 | 17.2 |
| Hct$^b$% | 47. | 47 |
| | 49 | 49 |
| | 42 | 41 |
| | 46 | 45 |
| | 48 | 48 |
| MCV$^c$ | 83 | 82 |
| | 85 | 84 |
| | 81 | 79 |
| | 83 | 83 |
| | 87 | 89 |
| MCH$^d$dpg | 28 | 29 |
| | 27 | 27 |
| | 30 | 30 |
| | 31 | 30 |
| | 31 | 33 |
| Granulocyte % | 65 | 68 |
| | 59 | 58 |
| | 47 | 47 |
| | 61 | 60 |
| | 65 | 65 |
| Lymphocyte % | 23 | 23 |
| | 25 | 26 |
| | 36 | 36 |
| | 34 | 35 |
| | 29 | 30 |

$^a$Hgb-hemoglobin.
$^b$Hct-hematocrit.
$^c$MCV-mean corpuscular volume.
$^d$MCH-mean corbpuscular hemoglobin.

EXAMPLE XXII

HIV ELISA Interference

In order to determine the effect of the composition on an HIV ELISA assay, an established 20-member reference panel was treated with 50 μL of the composition per mL and assayed alongside an untreated panel using the Biotech/DuPont (Rockville, Md.) HIV ELISA system. The optical densities of treated and untreated sera were very similar with an average ratio of treated-to-untreated of 1.03. A linear regression of the optical densities (O.D.s) yielded a slope of 1.00 with a y-intercept of 0.00 indicative of very close alignment. Both the treated and untreated panels matched the official panel designations.

EXAMPLE XXIII

Routine Blood Chemistries

Blood samples collected in red-topped tubes for routine chemistry were allowed to clot and were centrifuged to obtain serum. The eight samples used for the study were clear with no apparent hemolysis or lipid content. To one of two tubes containing 3 mL of serum, 20 μL of the composition were added (see composition A of Example XIV). Both tubes were mixed by vortex before analysis for CBC. The results presented in Table XIII reveal no differences in values with or without the composition. Paired t-tests run on the results indicate no differences in population at the 0.05 level.

TABLE XIV

Effect of the Composition on blood chemistries

| Test analyte name | Value after treatment with Compos. | Value without Compos. (Control) |
|---|---|---|
| Inorganic phosphate | 2.9 | 3.7 |
| | 4.5 | 4.4 |
| | 6.1 | 6.1 |
| | 5.0 | 5.1 |
| | 2.8 | 2.9 |
| | 3.0 | 2.8 |
| | 3.1 | 3.3 |
| Triglycerides | 261 | 298 |
| | 450 | 455 |
| | 341 | 330 |
| | 253 | 262 |
| | 281 | 287 |
| | 478 | 491 |
| | 291 | 280 |
| Uric acid | 2.7 | 2.6 |
| | 3.2 | 3.1 |
| | 2.7 | 2.7 |
| | 2.0 | 2.0 |
| | 3.0 | 3.1 |
| | 3.1 | 3.0 |
| | 3.5 | 3.5 |
| LDH$^a$ | 329 | 371 |
| | 300 | 309 |
| | 410 | 410 |
| | 581 | 560 |
| | 273 | 280 |
| | 350 | 353 |
| | 320 | 314 |
| SGOT$^b$ | 24 | 21 |
| | 12 | 14 |
| | 16 | 16 |
| | 19 | 18 |
| | 23 | 24 |
| | 20 | 20 |
| | 16 | 18 |
| SGPT$^c$ | 12.1 | 11.3 |
| | 12.5 | 12.1 |
| | 17.0 | 17.0 |
| | 9.0 | 9.6 |
| | 9.0 | 8.0 |
| | 12.0 | 12.0 |
| | 9.8 | 9.0 |
| Calcium | 10.8 | 10.0 |
| | 9.7 | 9.8 |
| | 9.5 | 9.5 |
| | 11.5 | 11.1 |
| | 8.2 | 8.2 |
| | 8.5 | 8.7 |

TABLE XIV-continued

Effect of the Composition on blood chemistries

| Test analyte name | Value after treatment with Compos. | Value without Compos. (Control) |
|---|---|---|
| | 9.8 | 9.5 |
| Glucose | 96 | 89 |
| | 117 | 109 |
| | 80 | 71 |
| | 90 | 94 |
| | 144 | 144 |
| | 83 | 80 |
| | 90 | 85 |
| Urea-nitrogen | 14.0 | 14.2 |
| | 6.8 | 7.0 |
| | 7.5 | 8.9 |
| | 14.1 | 13.3 |
| | 13.0 | 12.8 |
| | 17.1 | 17.1 |
| | 5.8 | 5.1 |
| Bilirubin total | 0.8 | 0.8 |
| | 1.3 | 1.2 |
| | 1.0 | 1.0 |
| | 2.4 | 3.8 |
| | 0.4 | 0.4 |
| | 0.8 | 0.6 |
| | 1.7 | 1.7 |
| Creatinine | 1.1 | 1.0 |
| | 0.4 | 0.3 |
| | 0.2 | 0.2 |
| | 0.3 | 0.4 |
| | 0.8 | 0.8 |
| | 1.5 | 1.6 |
| | 0.9 | 1.1 |
| Cholesterol | 184 | 174 |
| | 317 | 310 |
| | 209 | 210 |
| | 371 | 360 |
| | 180 | 184 |
| | 206 | 191 |
| | 218 | 252 |
| Protein total | 7.2 | 7.2 |
| | 7.1 | 7.1 |
| | 7.1 | 6.9 |
| | 7.8 | 7.8 |
| | 7.1 | 7.2 |
| | 7.1 | 7.0 |
| | 7.8 | 8.0 |
| Alkaline phosphatase | 8.1 | 9.8 |
| | 11.8 | 11.2 |
| | 13.9 | 14.1 |
| | 7.5 | 7.5 |
| | 24.0 | 21.0 |
| | 70.6 | 76.0 |
| | 18.2 | 19.1 |
| Total iron binding capacity | 317 | 309 |
| | 400 | 411 |
| | 501 | 480 |
| | 250 | 252 |
| | 313 | 320 |
| | 430 | 415 |
| | 386 | 371 |

[a]LDH-lactate hydrogenase.
[b]SGOT-serum glutamic-oxaloacetic transaminase.
[c]SGPT-serum glutamic-pyruvic transaminase
C. = composition

EXAMPLE XXIV

Radioimmunoassays

In order to assess the effect of the composition on RIA tests, 10 $\mu$L of the composition (see composition A of Example XV) were added to one of two (generally) 1.0-mL portions of serum. Both samples were mixed well and run simultaneously with controls and other standards. Table XV presents some representative values obtained. No differences were observed in any of the results other than an acceptable coefficient of variation expected in most immunoassays. Paired t-tests run on the parameters containing five or more observations indicated no differences in population at the 0.05 level.

TABLE XV

Effect of the Composition on RIA tests

| Test analyte name | Value after treatment with Composit. | Value without Composit. (control) |
|---|---|---|
| T-4 | 7.7 | 7.6 |
| | 22.0 | 21.2 |
| | 4.8 | 4.8 |
| | 9.2 | 9.2 |
| | 13.4 | 14.1 |
| | 5.1 | 4.9 |
| | 10.7 | 10.6 |
| | 13.0 | 13.0 |
| T-3 | 114 | 111 |
| | 209 | 161 |
| | 127 | 121 |
| | 136 | 143 |
| | 179 | 186 |
| | 83 | 80 |
| | 111 | 107 |
| | 174 | 168 |
| TSH[a] | 3.8 | 4.3 |
| | 0.6 | 0.6 |
| | 3.1 | 3.2 |
| | 0.8 | 0.8 |
| | 1.3 | 1.4 |
| | n.8 | 0.8 |
| | 1.8 | 1.9 |
| | 6.8 | 6.0 |
| Estriol | 13.8 | 13.0 |
| | 2.6 | 2.8 |
| | — | — |
| | 6.8 | 6.6 |
| | — | — |
| | — | — |
| | — | — |
| | — | — |
| Cortisol | 14.2 | 14.1 |
| | 17.1 | 17.6 |
| | 7.6 | 7.6 |
| | 14.1 | 13.2 |
| | 9.1 | 9.2 |
| | 11.1 | 11.o |
| | 9.2 | 8.8 |
| | 4.4 | 4.2 |
| Dilantin | 7.6 | 8.1 |
| | — | — |
| | 7.9 | 7.8 |
| | — | — |
| | — | — |
| | 7.8 | 8.1 |
| | — | — |
| | — | — |
| LH[b] | 11.6 | 11.3 |
| | 2.1 | 2.1 |
| | 3.1 | 3.1 |
| | — | — |
| | 12.1 | 11.0 |
| | — | — |
| | — | — |

TABLE XV-continued

Effect of the Composition on RIA tests

| Test analyte name | Value after treatment with Composit. | Value without Composit. (control) |
|---|---|---|
| FSH[c] | 7.4 | 7.1 |
| | 3.7 | 3.1 |
| | 4.5 | 4.7 |
| | — | — |
| | — | — |
| | 6.8 | 6.8 |
| | — | — |
| | — | — |

[a]TSH-thyroid stimulating hormone.
[b]LH-luteinizing hormone.
[c]FSK-follicle stimulating hormone.

EXAMPLE XXV

Dipstick Test on Urine

Ten duplicate 10-mL samples of urine were subjected to the Ames 7 test. 20 μL of the composition (see composition A of Example XIV) were added to one of each of the duplicates. Then both tubes were mixed well by inversion before testing using the Ames strips. No difference in results was noted for any of the samples.

EXAMPLE XXVI

Coagulation Tests

Coagulation studies including activated partial thromboplastin time (aPTT), prothrombin time (PT), fibrinogen, platelet count, and clotting time reported in Table XVI were unaffected by the presence of 10 μL of the composition (see composition A of Example XIV) in 2 mL of whole blood. Paired-tests run on the results indicate no differences in population at the 0.05 level. In other tests, no effect of the composition was noted on routine blood bank procedures such as ABO, Rh, and Coombs tests.

Additional studies evaluated the PT, aPTT and activated recalcification time of platelet-rich plasma (ART). Data were also obtained on platelet aggregation tests.

TABLE XVI

TABLE XVI-continued

Effect of the composition on coagulation tests

| Test analyte name | Value after treatment with the Compos. | Value without the Compos. (control) |
|---|---|---|
| PT (sec) | 13 | 11 |
| | 11 | 10 |
| | 8 | 8 |
| | 12 | 11 |
| | 10 | 10 |
| | 12 | 12 |
| Prothrombin factor II (sec) | 16 | 16 |
| | 16 | 15 |
| | 14 | 14 |
| | 15 | 16 |
| | 13 | 13 |
| | 11 | 11 |
| Factor VII fibrinogen mg/dL | — | — |
| | 230 | 217 |
| | 218 | 219 |
| | 252 | 240 |
| | 289 | 291 |
| | 252 | 246 |
| | 300 | 317 |
| Platelet count × 1000 | 178 | 173 |
| | 218 | 210 |
| | 142 | 141 |
| | 420 | 411 |
| | 460 | 462 |
| | 370 | 372 |
| Clotting time (min) | 9.8 | 9.8 |
| | 7.6 | 7.6 |
| | 8.3 | 8.1 |
| | 8.0 | 8.0 |
| | 9.0 | 8.9 |
| | 9.3 | 9.4 |

In order to carry out the experiment, venous blood was collected in one-tenth volume 0.129 M buffered citrate solution (Becton Dickinson, Vacutainer Systems, Rutherford, N.J.) from patients for coagulation assessment. All routine tests were performed in duplicate on the Fibrometer (BBL, Div. of Becton Dickinson). Prothrombin time was determined using thromboplastin-C (Dade, Miami, Fla.). Activated partial thromboplastin time was performed using Coag-a-chek kaolin reagent (Technicon Corp., Tarrytown, N.Y., originally manufactured by Hyland). The ART was assayed according to the method of Hunter and Allensworth (Hunter et al., *J. Clin. Path.* 20:244 (1967) and Hill et al., *Texas Medicine* 66:54 (1970)). Platelet aggregation studies were performed on a Sienco dual channel aggregation meter (Morrison, Colo.). Final concentration of the agonists were tested 1.2 and 1.5 mg/mL Ritocetinn (Bio/Data Corp., Hatboro, Pa.), 100 and 1 μm ADP (Sigma Grade I.), and 5 μg/mL collagen (Chrono-Log Corp., Havertown, Pa.).

Each plasma sample was divided into two aliquots of 1.0–2.5 mL. One aliquot served as a control; 10 μL of the composition was added to the other aliquot. (The recommended procedure of adding one drop or 20 μL of the composition to 7–15 mL of whole blood would have necessitated the drawing of more blood than is normal practice.) The paired samples were than assayed for PT, aPTT, ART, or platelet aggregation response.

For testing the effect of the composition on plasma after freezing, plasma samples were treated with the agent and assayed for PT and aPTT. The plasmas were frozen at −20° C. for approx. 1 hr, thawed quickly at 37° C., and the assays repeated. Results for the paired samples were evaluated using Statpro (Penton Software, Inc., New York, N.Y.).

Table XVII summarizes the effect of the composition on the PT, aPTT, and ART. The correlation of the paired plasma samples by linear regression analysis (untreated plasma as the independent variable) was quite good with $r^2$ values of 0.94–0.98. The Wilcoxon signed rank test for matched pairs indicated no significant differences between the samples of the PT and aPTT measurements.

The ART data revealed a small (average 1.5 sec) but significant ($p<0.01$) shortening of the clot time. (At the reduced blood and virucide volumes actually used, the composition concentration in the sample was 3–4 times that recommended by the manufacturer.) The detergents in the composition may have facilitated the release of platelet factor 3, an integral part of this screening test.

Table XVIII shows the analysis of results obtained on plasmas treated with the the composition before and after freezing of the plasma. No effect was induced by the composition.

Table XIX lists the platelet aggregation results obtained. Although limited in quantity, the data indicate no apparent effect on the composition on the results. The collagen lag phase, the time elapsed between the addition of collagen and the commencement of aggregation, was the same in the presence or absence of the composition. A complete evaluation awaits further comparison, with particular emphasis on samples from patients with impaired platelet function.

TABLE XVII

Paired plasma samples with or without the addition of the composition

|  | PT | aPTT | ART |
|---|---|---|---|
| Number | 19 | 17 | 14 |
| Range (sec) | 11.4–16.8 | 23.6–63.4 | 31.2–53.1 |
| Linear regression |  |  |  |
| $r^2$ | 0.9563 | 0.9602 | 0.9378 |
| Slope | 0.8829 | 0.9240 | 0.9123 |
| Intercept | 1.2 | 2.2 | 1.9 |
| Wilcoxon signed rank |  |  |  |
| T score for + ranks | 85 | 86 | 96 |
| T score for − ranks | 78 | 66 | 8 |
| Probability | >0.1 | >0.1 | <0.01 |

TABLE XVIII

Plasma samples with the composition before and after freezing

|  | PT | aPTT |
|---|---|---|
| Number | 11 | 11 |
| Range (sec) linear regr. | 12.0–23.6 | 25.0–82.0 |
| Linear regression |  |  |
| $r^2$ | 0.9909 | 0.9958 |
| Slope | 1.0238 | 1.0115 |
| Intercept | −0.5 | 0.2 |
| Wilcoxon signed rank |  |  |
| T score for + ranks | 47 | 11 |
| T score for − ranks | 16 | 55 |
| Probability | >0.1 | >0.1 |

TABLE XVIV

Platelet aggregation results with or without the addition of the composition

|  | Without | With |
|---|---|---|
| 100 µm ADP* | 86% | 81% |
|  | 71 | 71 |
|  | 73 | 85 |
| 1 µm ADP | 11 | 12 |
|  | 4 | 4 |
| Collagen | 71 | 79 |
|  | 79 | 81 |
|  | 46 | 50 |
| Ristocetin, 1.2 mg/mL | 78 | 81 |
| 1.5 mg/mL | 80 | 86 |

*ADP - adenosine diphosphate

What is claimed is:

1. A composition for use in the disinfection of a blood or blood component sample, wherein said sample is contained in a blood bag and wherein said composition controls hemolysis of and maintains the chemical and physical characteristics of the cells present in said sample such that said sample can be used for a transfusion, said composition consisting essentially of, in combination, an anionic surfactant, at least one non-anionic surfactant, a stabilizer, and a buffer solution.

2. The composition of claim 1 wherein said physical and chemical characteristics which are maintained are selected from the group consisting of hemoglobin content, red blood cell count, mean corpuscular volume, and red cell membrane structure.

3. The composition of claim 1 wherein said anionic surfactant is a lauryl ether, said at least one non-anionic surfactant is an oxyethylated alkylphenol, said stabilizer is a sugar, and said buffer solution comprises two salts and two phosphates.

4. The composition of claim 3 wherein said lauryl ether is Brij-35, said at least one non-anionic surfactant is selected from the group consisting of Nonidet-P 40 and Nonoxynol-9, said sugar is sucrose, said two salts are KCl and NaCl, and said phosphates are $Na_2HPO_4$ and $KH_2PO_4$.

5. The composition of claim 4 wherein said Brij-35 is present in a concentration of about 0.05–4%, said Nonidet-P 40 and/or Nonoxynol-9 is present in a concentration of about 0.05–4%, said sucrose is present in a concentration of 0.01–5.0%, said NaCl is present in a concentration of concentration of 0.4–5.0%, said KCl is present in a concentration of 0.01–5%, and said $Na_2HPO_4$ and $KH_2PO_4$ are each present in a concentration of 0.1–5%.

6. The composition of claim 5 wherein said Brij-35 is present in a concentration of about 0.5–1.5, said Nonidet-P 40 and/or Nonoxynol-9 is present in a concentration of about 0.5–1.5%, said sucrose is present in a concentration of about 0.03–1%, said NaCl is present in a concentration of about 0.5–1.5%, said KCl is present in a concentration of about 0.02–1.0% and said $Na_2HPO_4$ and $KH_2PO_4$ are each present in a concentration of about 0.01–5%.

7. The composition of claim 6 wherein said Brij-35 is present in a concentration of about 1%, said Nonidet-P 40 and/or Nonoxynol-9 is present in a concentration of about 1.0%, said sucrose is present in a concentration of about 0.05%, said NaCl is present in a concentration of about 0.90%, said KCl is present in a concentration of about 0.04%, and said $Na_2HPO_4$ and $KH_2PO_4$ are each present in a concentration of about 0.1%.

8. A method of disinfecting a blood sample or blood component sample comprising, adding to said sample contained in a blood bag, an amount of the composition of claim 7 sufficient to effect said disinfection.

9. A method of disinfecting a blood sample or blood component sample contained in a blood bag, consisting essentially of the combination of steps of:
   a) introducing the disinfectant composition of claim 8 into a blood bag containing blood or a component thereof;
   b) mixing said composition with said blood or blood component sample at regular intervals in order to induce contact between the sample and the composition;
   c) separating the cellular components from the supernatant wherein said supernatant contains non-cellular components; and
   d) subjecting residual material to an extraction technique for a sufficient number of times effective for removal of remaining disinfectant composition components not separated in step (c).

10. The method of claim 9 wherein said separation of step (c) is effected by filtration, centrifugation or decantation.

11. The method of claim 9 wherein said extraction technique of step (d) is an immunological, washing or chromatographic technique.

12. The method of claim 9 wherein said gram negative bacteria is *Yersinia enterocolitica*.

13. The method of claim 9 wherein said contact between said sample and said composition occurs at room temperature.

14. The method of claim 9 wherein said contact between said sample and said composition occurs for a minimum required time of at least two minutes.

15. The method of claim 9 wherein said blood component is plasma.

16. A disinfected blood or blood component sample produced according to the method of claim 9.

17. The method of claim 9 further comprising the steps of: e) adding a preservative solution to the product of step (d); and f) storing the resulting product of step (e) at a low temperature.

18. The method of claim 17 wherein the resulting product of step (f) may be infused into a mammal.

19. The method of claim 18 wherein said mammal is a human.

* * * * *